US00PP13572P2

(12) United States Plant Patent
Moerman

(10) Patent No.: US PP13,572 P2
(45) Date of Patent: Feb. 18, 2003

(54) ASTER PLANT NAMED 'MOERCASSINO'

(75) Inventor: Marcel Moerman, De Lier (NL)

(73) Assignee: Moerselect B.V., De Lier (NL)

( * ) Notice: Subject to any disclaimer, the term of this patent is extended or adjusted under 35 U.S.C. 154(b) by 0 days.

(21) Appl. No.: 10/099,244

(22) Filed: Mar. 15, 2002

(51) Int. Cl.[7] ..... A01H 5/00

(52) U.S. Cl. ..... Plt./355

(58) Field of Search ..... Plt./355

*Primary Examiner*—Kent L. Bell
(74) *Attorney, Agent, or Firm*—C. A. Whealy

(57) ABSTRACT

A distinct cultivar of Aster plant named 'Moercassino', characterized by its rapid growth rate; numerous inflorescences per flowering stem; white-colored ray florets; yellow-colored disc florets; and good postproduction longevity.

1 Drawing Sheet

BOTANICAL CLASSIFICATION/CULTIVAR DESIGNATION

*Aster novi-belgii* cultivar 'Moercassino'.

BACKGROUND OF THE INVENTION

The present Invention relates to a new and distinct cultivar of Aster plant, botanically known as *Aster novi-belgii* and referred to by the cultivar name 'Moercassino'.

The new Aster is a product of a planned breeding program conducted by the Inventor in De Lier, The Netherlands. The objective of the breeding program was to develop new strong-growing cut flower Aster cultivars with attractive floret colors. The new Aster originated from a cross made by the Inventor of a proprietary Aster selection identified as code number 280, not patented, as the female, or seed, parent with a proprietary Aster selection identified as code number 2267, not patented, as the male, or pollen, parent.

Asexual reproduction of the new cultivar by terminal cuttings taken in De Lier, The Netherlands has shown that the unique features of this new Aster are stable and reproduced true to type in successive generations.

SUMMARY OF THE INVENTION

The following traits have been repeatedly observed and are determined to be the unique characteristics of 'Moercassino'. These characteristics in combination distinguish 'Moercassino' as a new and distinct cultivar:

1. Rapid growth rate.
2. Numerous inflorescences per flowering stem.
3. White-colored ray florets and yellow-colored disc florets.
4. Good postproduction longevity.

Plants of the new Aster differ from plants of the female parent, the selection 280, in the following characteristics:

1. Plants of the new Aster have larger leaves than plants of the selection 280.
2. Plants of the new Aster have longer flowering stems than plants of the selection 280.
3. Plants of the new Aster have larger inflorescences than plants of the selection 280.
4. Plants of the new Aster and the selection 280 differ in disc floret coloration.

Plants of the new Aster differ from plants of the male parent, the selection 2267, in the following characteristics:

1. Plants of the new Aster have larger leaves than plants of the selection 2267.
2. Plants of the new Aster have larger inflorescences than plants of the selection 2267.
3. Plants of the new Aster and the selection 2267 differ in disc floret coloration.

Plants of the new Aster can be compared to plants of the Aster cultivar 'Monte Cassino', not patented. In side-by-side comparisons conducted in De Lier, The Netherlands, plants of the new Aster differed from plants of the cultivar 'Monte Cassino' in the following characteristics:

1. Plants of the new Aster grew more rapidly than plants of the cultivar 'Monte Cassino'.
2. Plants of the new Aster had larger leaves than plants of the cultivar 'Monte Cassino'.
3. Plants of the new Aster had larger inflorescences than plants of the cultivar 'Monte Cassino'.
4. Plants of the new Aster and the cultivar 'Monte Cassino' differed in disc floret coloration.

BRIEF DESCRIPTION OF THE PHOTOGRAPH

The accompanying colored photograph illustrates the overall appearance of the new Aster, showing the colors as true as it is reasonably possible to obtain in colored reproductions of this type. Colors in the photograph may differ slightly from the color values cited in the detailed botanical description which accurately describe the actual colors of the new Aster.

The photograph comprises a side perspective view of a typical flowering stem of the new Aster.

DETAILED BOTANICAL DESCRIPTION

The cultivar 'Moercassino' has not been observed under all possible environmental conditions. The phenotype may vary somewhat with variations in environment such as temperature, daylength, and light intensity, without, however, any variance in genotype.

The aforementioned photograph, following observations, measurements and values describe flowering plants of the new Aster grown in De Lier, The Netherlands, under conditions which approximate commercial cut Aster production in a glass-covered greenhouse. Plants used in the photographs and the description were grown during the summer and were about 13 weeks old. During the production of the plants, day and night temperatures averaged 18° C. and light levels averaged 6,000 lux. Color references are made to The Royal Horticultural Society Colour Chart, 1995 Edition, except where general terms of ordinary dictionary significance are used.

Botanical classification: *Aster novi-belgii* cultivar 'Moercassino'.

Parentage:

*Female, or seed, parent.*—Proprietary selection of *Aster novi-belgii* identified as code number 280, not patented.

*Male, or pollen, parent.*—Proprietary selection of *Aster novi-belgii* identified as code number 2267, not patented.

Propagation:

*Type.*—By terminal cuttings.

*Time to initiate roots, summer.*—About 10 days at 18° C.

*Time to initiate roots, winter.*—About 12 days at 18° C.

*Time to develop roots, summer.*—About 14 days at 18° C.

*Time to develop roots, winter.*—About 21 days at 18° C.

*Rooting habit.*—Fine, freely branching; white in color.

Plant description:

*Appearance.*—Herbaceous flowering plant used for cut flowers. Stems upright; basally branching; flowering stems, pyramidal in overall shape. Very freely flowering with numerous inflorescences per flowering stem; white-colored ray florets and yellow-colored disc florets.

*Crop time.*—Strong, rapid growth rate; from planting rooted cuttings, about 13 weeks are required to harvesting of flowering stems.

*Branching habit.*—Freely branching; typically about five lateral branches develop after pinching (removal of terminal apex).

*Plant height.*—About 1 meter.

*Plant diameter or spread.*—About 25 cm.

*Lateral branches (flowering).*—Length: About 80 cm. Diameter or spread: About 10 cm. Internode length: About 2.75 cm. Texture: Glabrous, smooth. Color: 137B.

*Foliage description.*—Leaves alternate, single; sessile. Length: About 12 cm. Width: About 1 cm. Shape: Roughly lanceolate. Apex: Pointed. Base: Attenuate. Margin: Slightly serrated. Texture, upper and lower surfaces: Smooth. Color: Young and fully expanded foliage, upper surface: 137A; venation, 137A. Young and fully expanded foliage, lower surface: 137B; venation, 137B.

Inflorescence description:

*Appearance.*—Composite inflorescence form. Disc and ray florets arranged acropetally on a capitulum. Inflorescences displayed upright on peduncles arising from upper leaf axils. Floriferous with more than 150 inflorescence buds and open inflorescences per flowering stem.

*Flowering response.*—Short day responsive; under natural photoperiodic conditions, plants flower in the autumn. Flowering can be induced under short day/long night conditions at other times of the year. Response time is about 6.5 weeks.

*Post-production longevity.*—Inflorescences last about 2.5 weeks as a cut flower and about 2.5 weeks on the plant. Inflorescences persistent.

*Fragrance.*—None detected.

*Inflorescence bud.*—Length: About 4 mm. Diameter: About 3 mm. Shape: Oblong. Time to opening: About three days. Color: 137B.

*Inflorescence size.*—Diameter: About 2 cm. Depth (height): About 1 cm. Diameter of disc: About 6 mm.

*Ray florets.*—Number of rows: Typically one per inflorescence. Length: About 1 cm. Width: About 3 mm. Shape: Oblong. Apex: Pointed. Base: Attenuate. Margin: Entire. Aspect: Mostly flat. Texture, upper and lower surfaces: Smooth, satiny. Color: When opening and fully opened, upper surface: 155D. When opening and fully opened, lower surface: 155D.

*Disc florets.*—Shape: Tubular. Number of disc florets per inflorescence: About 60. Length: About 5 mm. Diameter: About 1 mm. Color: Immature: 6B. Mature: 8B.

*Phyllaries.*—Shape: Linear. Apex: Pointed. Margin: Entire. Texture, upper and lower surfaces: Smooth. Color, upper and lower surfaces: 137B.

*Peduncle.*—Aspect: Angled about 45° to the stem. Strength: Strong. Texture: Smooth. Color: 137B.

*Reproductive organs.*—Androecium: Present on disc florets only. Anther color: Close to 6A. Pollen: None observed. Gynoecium: Present on ray and disc florets. Stigma color: Close to 6A.

*Seed/fruit.*—Seed and fruit development has not been observed.

Disease/pest resistance: Resistance to pathogens and pests common to Aster has not been observed on plants of the new Aster.

It is claimed:

1. A new and distinct cultivar of Aster plant named 'Moercassino', as illustrated and described.

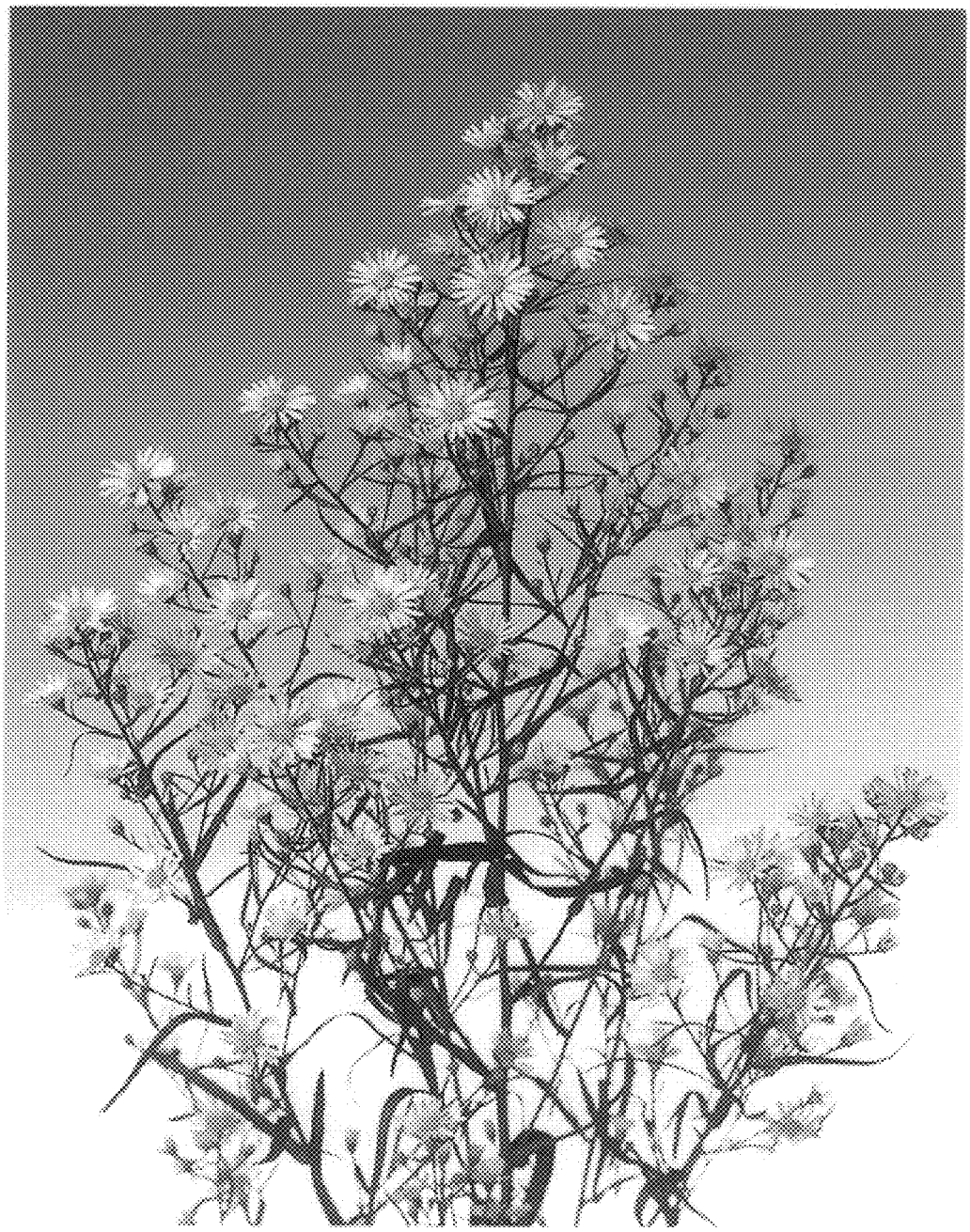

* * * * *